United States Patent [19]
Dreher et al.

[11] Patent Number: 4,566,585
[45] Date of Patent: Jan. 28, 1986

[54] SELF-CENTERING DRIVER FOR OBLONG MATERIAL

[75] Inventors: Ulrich Dreher, Trochtelfingen; Helmut Reitz, Metzingen, both of Fed. Rep. of Germany

[73] Assignee: Institut Dr. Friedrich Förster, Reutlingen, Fed. Rep. of Germany

[21] Appl. No.: 500,364

[22] Filed: Jun. 2, 1983

[30] Foreign Application Priority Data

Feb. 16, 1983 [DE] Fed. Rep. of Germany ....... 3222104

[51] Int. Cl.[4] .............................................. B65G 29/00
[52] U.S. Cl. ..................................... 198/624; 198/627
[58] Field of Search ....................... 198/624, 627, 628; 144/246 R; 72/97, 209

[56] References Cited

U.S. PATENT DOCUMENTS

| | | | |
|---|---|---|---|
| 2,679,871 | 6/1954 | Ford | 144/246 R |
| 3,050,178 | 8/1962 | Stone | 198/834 |
| 3,228,439 | 1/1966 | Jonsson et al. | 144/246 R |
| 3,596,690 | 8/1971 | Hamilton | 144/246 R |
| 3,844,398 | 9/1974 | Pinat | 198/628 |

FOREIGN PATENT DOCUMENTS

| | | | |
|---|---|---|---|
| 1553515 | 1/1969 | France | 198/624 |
| 1269948 | 6/1972 | United Kingdom | 198/627 |

Primary Examiner—Joseph E. Valenza
Assistant Examiner—Kyle E. Shane
Attorney, Agent, or Firm—George J. Netter

[57] ABSTRACT

A driver for oblong material having three arms carrying the driving elements which swing vertically with respect to the material path of movement. For a selected setting angle of the arms, the point of contact of a driving roller with the material is displaced such that, on the diameter of the test material becoming smaller, the point of contact is moved towards the edge of the roller. This feature has three desirable consequences: First, wear is not concentrated on a single track of the roller surface; second, the pressing-on force of the rollers is decreased with the decreasing diameter of the test material; and third, when using three rollers, the seeing angle can be adjusted such that for the narrowest approach of the rollers possible, one edge each of a roller meets with the respective edges of the other rollers in one point.

9 Claims, 5 Drawing Figures

SELF-CENTERING DRIVER FOR OBLONG MATERIAL

The invention relates to a driver for self-centering driving of oblong-semi-finished material of cylindrical or polygonal cross-section along a track parallel to the material longitudinal axis.

BACKGROUND

Drivers are needed for the transportation of oblong test samples through a material testing device, such as eddy-current or stray-flux testing equipment, where it is important to have within a relatively large diameter range, uniform axial movement of the test samples and to be able to guide them accurately along a given track through the testing device, irrespective of diameter variations or cross movement of the driven material.

A driver for this purpose is known which has three arms movable over a lifting spindle in radial direction of the test material and exhibiting at their front end each a fork accommodating a driving roller. The axles of the driving rollers are driven by a common geared motor through drive shafts, the upper roller for space reasons, requiring an additional miter gear. The lifting spindles are actuated by a common control mechanism. The disadvantage of such a driver is that the three drive shafts are arranged in different directions outwards and terminate at positions remote from each other. Their common drive, therefore, requires a complicated and expensive gear arrangement. Another disadvantage is that for radially set rollers, the useful diameter range is restricted with respect to small diameter test material for the rollers cannot come together sufficiently close enough, even when a sharp-angled roller profile is used instead of the more typical right-angle profile. A further disadvantage is that a common actuation of three lifting spindles located relatively remote from each other is not possible without appreciable mechanical effort.

SUMMARY OF DESCRIBED EMBODIMENTS

In accordance with the described invention a driver is provided in which the moving energy is brought forward to the driving elements and the simultaneous adjustment of the driving elements in a simple manner with respect to the semi-finished material is possible. The driver has a simple and space-saving construction in that the arms carrying the driving elements may be relatively short, and the driver does not need large dimensions in the radial direction. The driver arms swing vertically to the moving direction so that the over-all length in the axial direction can also be kept extremely small. For a selected setting angle of the arms, the point of contact of a roller with the semi-finished material is displaced such that, on the diameter of the test material becoming smaller, the point of contact is moved towards the edge of the roller. This latter feature has three desirable consequences: First, wear is not concentrated on a single track of the roller surface; second, the pressing-on force of the rollers is decreased with decreasing diameter of the test material; and third, when using three rollers, the setting angle can be adjusted such that for the narrowest approach of the rollers possible, one edge each of a roller meets with the respective edges of the other rollers in one point.

The shafts are provided for bringing forward the moving energy for the driving elements parallel to each other. This results in very simple means for their driving.

Another advantage of the described driver is that it enables common adjustment of the arms carrying the driving elements.

DESCRIPTION OF PREFERRED EMBODIMENTS

Figure 1:
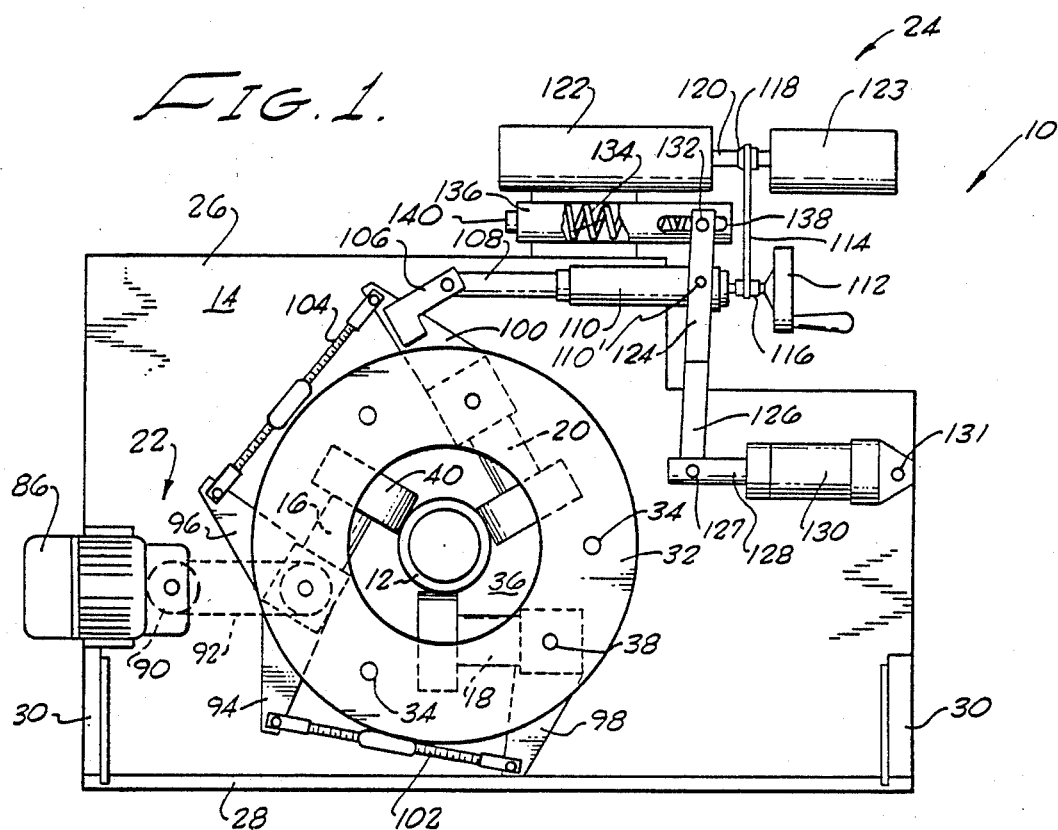
FIG. 1 depicts the front elevational view of a drive having three driving arms.
Figures 2, 3:
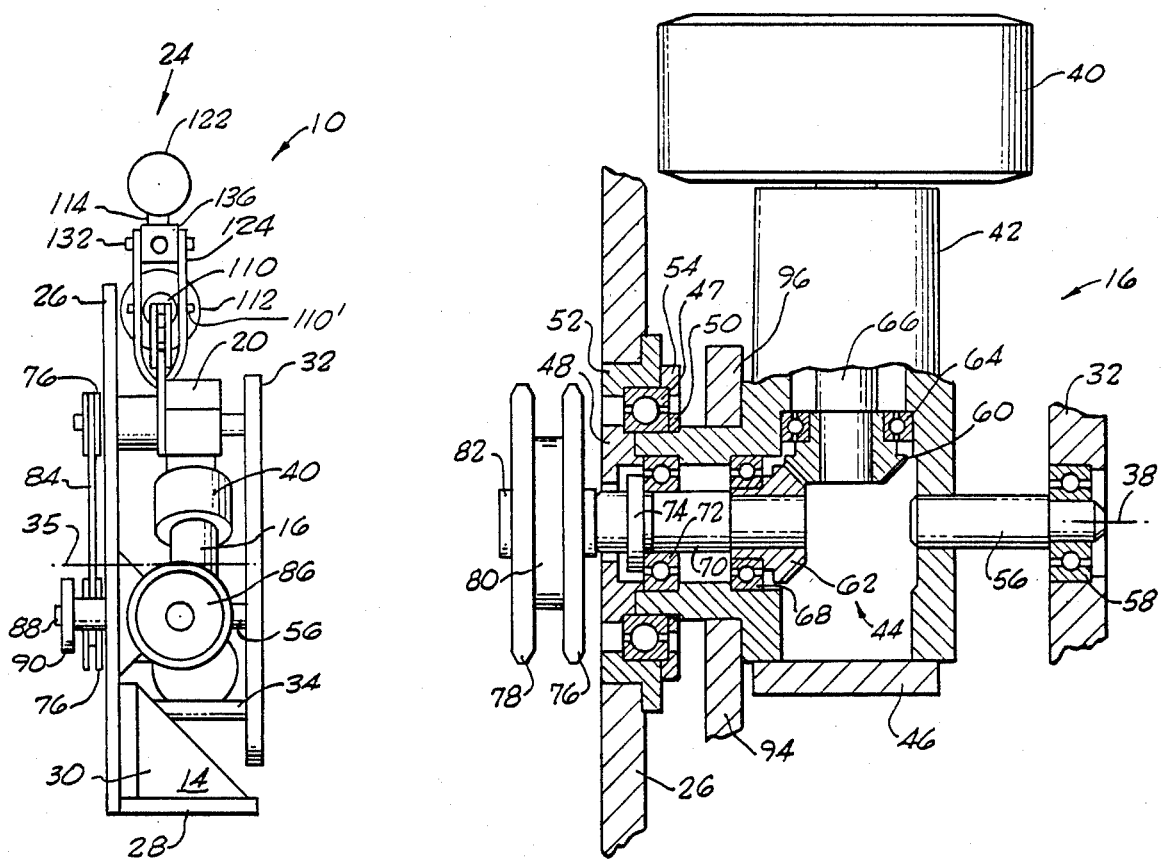
FIG. 2 shows a side elevational view of the driver.
FIG. 3 depicts a side elevational, sectional view of a driving arm.

The driver 10 shown in FIGS. 1 and 2, in front and side views respectively, serves for moving semi-finished elongated or oblong material, such as a tube 12, with uniform speed through certain devices, particularly those for non-destructive material testing. The driver can be divided generally into a mounting body 14, three basically identical driving arms 16, 18, 20, a driving power source 22 for the driving arms, and an adjustment device 24 for the arms.

The mounting body 14 includes a mounting plate 26, a base plate 28, two stiffening angles 30, each welded to the mounting plate, and a mounting ring 32 rigidly fastened to the mounting plate by a pin 34. Mounting plate 26 as well as mounting ring 32 each have a circular opening as a passageway for the test material 12.

The three driving arms 16, 18, 20 are held at an angular distance of 120 degrees between the mounting plate 26 and the mounting rings 32 and can be swung in a plane vertical to the track 35 of the semi-finished material about an axis of rotation 38. In principle, it is sufficient to drive only one of the rotation elements, in the present case of the rollers 40.

The advantage of the method used in the example to drive all rollers 40 is that the force to be transferred is larger, the wear of the contact surfaces smaller as well as more uniform, and the running is smoother. For rollers 40 not being driven, one would have to accept that they are accelerated unevenly by any arriving semi-finished material to the speed of the driven roller. The rollers 40 may be made from any suitable metal. For improvement of the friction and damping of vibrations, the rolling surface of the rollers can be provided with a coating exhibiting desired elastic properties.

One of the driving arms 16 is shown in FIG. 3 in an enlarged view. A housing 42 can be seen, containing inside a miter gear 44 sealed by a plate 46. The housing 42 is connected to the mounting plate 26 over a roller bearing 47. For the fixation of the bearing 47 to the housing a ring 48 and a disk 50 serve. For the fixation of the bearing 47 to the mounting plate 26, a bearing bed 52 and a bearing ring 54 are used. On the opposite side, the housing 42 is supported by a bolt 56 attached to the latter over a ball bearing 58 in the mounting ring 32. The miter gear 44 is composed of two bevel gears 60 and 62 engaged with each other. Bevel gear 60, borne in a ball bearing 64, drives the roller 40 over a shaft 66, and bevel gear 62 rests in a ball bearing 68 and is driven by a shaft 70, which, for its part, rests in a ball bearing 72. The latter is fixed to the housing 42 by the ring 48 and is screwed onto the shaft side by a threaded ring 74. At the outer end of shaft 70, two driving wheels 76 and 78 are arranged, being held together by a disk 80 and by a screw 82. For driving the rollers 40 over miter gear 44 and shafts 70 and 66, the driving wheels 76 of all driving arms 16, 18, 20 are connected to each other via a driving chain 84 such that it is sufficient for driving all rollers to rotate the driving wheel 78 of the driving arm 16 alone.

This motion is effected by the driving device 22, the active part of which is a miter-gear motor 86. Due to the type of construction of the latter, it is possible to get along with the given over-all length of the mounting body. The miter-gear motor 86 is attached to the mounting plate 26 and drives a driving wheel 90 about a shaft 88, this wheel being, for its part, driving the driving wheel 78 of driving arm 18 over a chain 92. For the remaining driving arms 18, 20, the driving wheel 78 may be omitted.

Besides the last mentioned fact, the driving arms 16, 18, 20 differ by having lever projections 94, 96, 98, 100 of different design, these projections being rigidly fixed to the housing 42. Thus lever projection 96 protrudes sidewards and lever 94 backwards from driver 16. For the driving arm 18, the lever projection 98 extending sidewards whereas lever 100 projects backwards from driving arm 20. The lever projections 94 and 96 are connected to the lever projections 98 and 100 by bar structures 102 and 104, engaging each at the same radius of the swing circle about the axis of rotation 38 and forcing, thus, all driving arms 16, 18, 20 into the same swinging movement, if one of them performs such a movement. In this way, the desired centering of the semi-finished material is made possible. Instead of connecting the driving arms 16 together, 18, 20 for actuating their adjustment by lever projections and bar structures to each other, this can also be effected, e.g., by use of chain wheels which are rigidly fixed to the housing 42, coaxial to the axis of rotation 38, these wheels being connected frictionally to each other by an endless chain. For adjustment, the chain or one of the chain wheels may be driven by an adjustment device.

The necessary pressing-on force for the rollers 40 as well as their adjustment and setting with respect to the test material is provided by the adjustment device 24. A lug 106 is rigidly fixed to the lever projection 100 of the driving arm 20 and coupled to the lifting arm 108 of spindle gearing 110. For actuation of the spindle gearing 110 and, thus, for adjustment of the rollers 40 to a desired diameter of the test material, a hand wheel 112 is provided connected via a toothed strap 114, toothed wheels 116, 118 (teeth on strap and wheels not shown) and a shaft 120 to adjusting drive 122. Rotation of wheel 112 via internal gearing extends (or retracts) arm 108 which adjustably positions rollers 40 with respect to tube 12. A transducer 123 can be connected to the adjusting drive 122 by the shaft 120. Its electrical signal delivers continuous information on the adjustment of the driving arms 16, 18, 20.

The lifting spindle 110 is pivoted about pin 110' in the fork 124 of a fork lever 126. At its lower end, the fork lever 126 is connected by a pin 127 to the lifting arm 128 of lifting cylinder 130, which, in turn, is pivoted with a shackle toggle joint 131 to the mounting plate 26. At its upper end, the fork lever 126 is connected to the compression spring 134 of a spring arrangement 136 by a pin 132, which is pushed to the right by the compression spring 134 and which, thus, effects, for a corresponding setting of the rollers 40, a continuous pressing-on of the rollers on the test material 12. The course of the pin 132 is limited by a stop 138, determining also the rest position of the rollers 40 in case no test material 12 is present. The pressing-on force of the spring arrangement 136 is adjustable by a screw 140, so that a roller pressing-on force can be selected guaranteeing, on one hand, a deformation of the semi-finished material 12, e.g. in the case of a thin-wall tube.

While the basic task of the pressure cylinder 130 is the setting of the rollers 40 over a short distance, it can also take over, moreover, the task of pressing the rollers on the test material 12, if need be. In this case, the spring arrangement 136 is not necessary any more and the pin 132 is provided with a fixed pivotable bearing. On the other hand, however, it is also possible, if a setting by the pressure cylinder 130 is to be omitted, to bear the lower end of the fork lever 126 by the pin 127 directly on the mounting plate 26.

Figure 4:
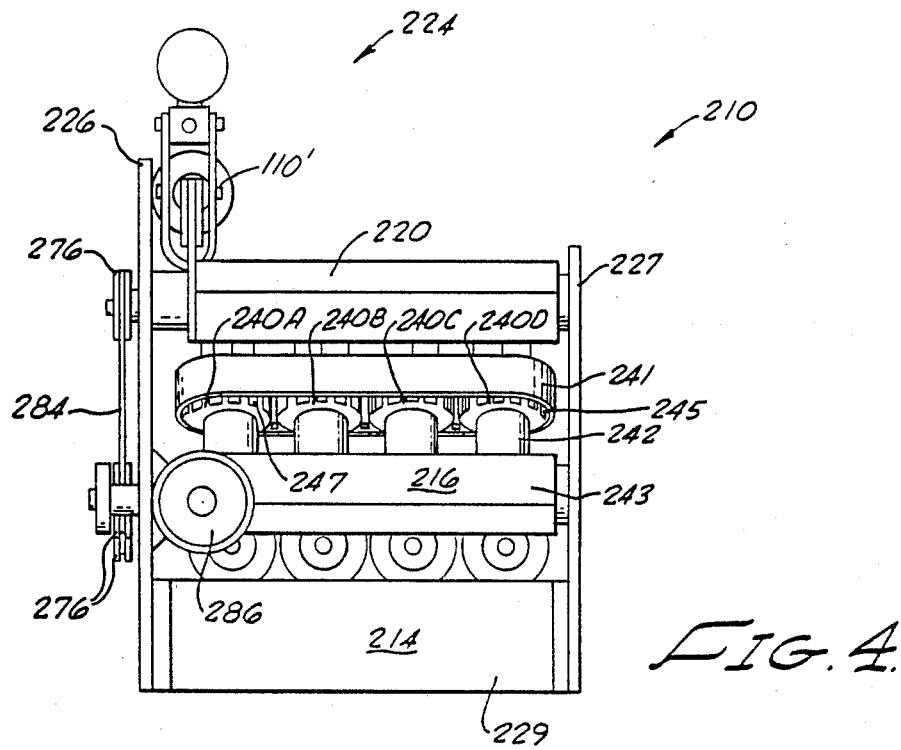
FIG. 4 illustrates a belt-driving arrangement.

An alternative embodiment of the invention shown in FIG. 4, here designated as a belt-driving device, is especially advantageous in three cases:

1. The test material is smooth and fouled by oil, so that steel rollers cannot provide the required driving forces;
2. The test material has a sensitive surface or does not allow high holding forces for stability reasons (e.g., thin-walled precision tubes); and
3. The device for testing the material 12 requires a particularly high vibration damping or the inlet roller bed excites vibrations to a high degree.

In the mentioned cases, by a belt-driving device 210, large driving forces, a precise self-centering guidance and a high degree of smoothness of running and vibration damping can be obtained. As seen from the front, the device 210 exhibits basically the same pattern as the driver 10 already described, so that reference can be made to the front view according to FIG. 1. The mounting body 214 consists basically of the mounting plate 226 and a reverse construction plate 227. The mentioned plates are held together by suitable components, of which, in FIG. 4, only a side plate 229 is shown. Between mounting plate 226 and construction plate 227, three driving arms 216, 218, 220 are mounted (only driving arm 216 is clearly visible), of which each exhibits four rollers 240A, 240B, 240C, and 240D. The latter are connected to a bar 243 over four bearing housings 242, this bar being mounted between plates 226 and 227 corresponds to the housing 42 in FIG. 3. The rollers 240A to 240D are surrounded by a rugged elastic endless driving belt 241. A lateral sliding-off of the driving-belt 241 can be prevented by disks placed at each side of roller 240 or by a corresponding shaping of the rollers. The required tension of the driving belt 241 is produced by a tension device (not shown). The driving belt 241 is provided with a tooth-shaped profile 245 engaging with corresponding teeth 247 of the rollers 240A, 240B, 240C, 240D, in order to provide a good force transfer. The rollers 240D act as guide rollers. The rollers 240B and 240C are used as supporting rollers and contribute to enabling a transfer of forces over as long a part of the belt as possible. Only the rollers 240A operate as driving rollers. In an analogous way to the principle shown in FIG. 3, they are driven by a miter gear, further via driving wheels 276, a driving chain 284, a driving chain 92, and the miter-gear motor 286. An adjustment device 224 may correspond to the adjustment device 24 in all details.

Figure 5:
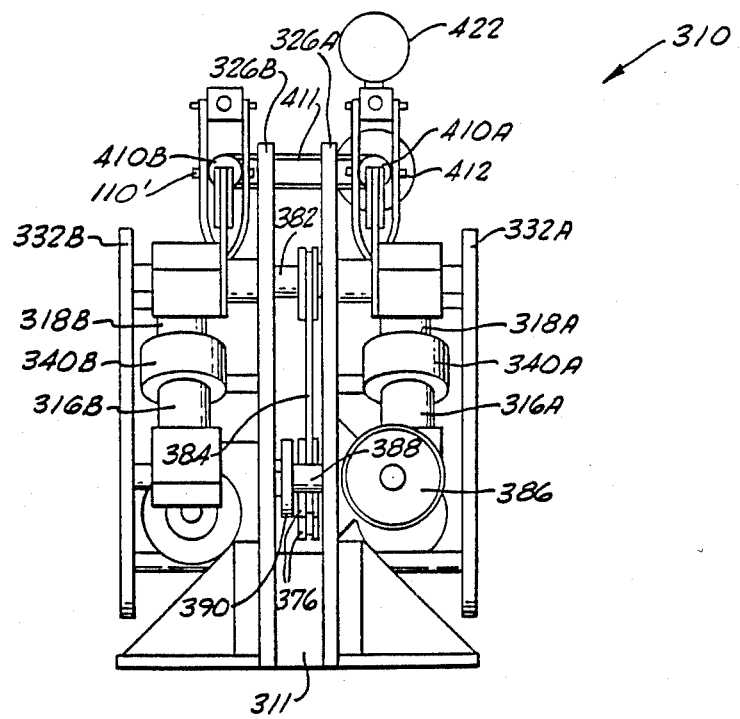
FIG. 5 depicts a double driver.

As another alternative embodiment of the invention, the double driver 310 shown in FIG. 5 shall be regarded. It is applied, when the driving forces generated by the simple driver 10 are not sufficient, without, however, meeting such high requirements as for the belt-driving device 210. The right half of the double driver 310 is, as can be seen from FIG. 5, basically identically constructed to the already described driver 10. Therefore, only what is different from the first embodiment will be described. Opposed to the driving arms 316A, 318A, 320A are arranged, at the left side of FIG. 5, symmetric driving arms 316B, 318B, 320B, being pivotable, as the first-mentioned driving arms, between plates 326B and 332B. The plates 326A and 326B are kept at the necessary distance by connection means, of which only connection plate 311 is shown. The shafts 382 of the driving arms 316A, 318A, 320A pass through and drive simultaneously the driving arms 316B, 318B, 320B. The miter gears in the driving arms 316B, 318B, 320B are connected in such a way that the rollers 340B run in the transportation device. Three driving wheels frictionally connected to the shafts 382 are surrounded by a driving chain 384 and are driven via a driving chain acting in an analogous manner to the driving chain 92 of FIG. 1, a driving wheel 390 and a shaft 388 by a miter-gear motor 386. For adjustment of the driving arms 316A, 318A, 320A or 316B, 318B, 320B, respectively, the same actuation means are provided. That is, lever projections and connecting bar structures (as shown in FIG. 1) extend further over a lug at lifting spindles 410A and 410B joined to one of the lever projections. As common drive for the lifting spindles 410A and 410B, a hand wheel 412 or an adjusting drive 422 is provided. The connection required for this is performed by a driving wheel on the driving shaft of the lifting spindle 410B, a driving strap 411, and an additional driving wheel on the driving shaft of the lifting spindle 410A.

We claim:

1. Driver for self-centering driver of oblong-shaped semifinished material of a cylindrical or polygonal cross section, said drive being in longitudinal direction of the material along a track, including a mounting body having a passage for the material being driven along the track, at least three arms attached to the mounting body, at the nearest part of the arms to the material one rotation element each is arranged, at least one of said rotation elements being driven and in driving contact with the material, and means for simultaneous and uniform adjustment of the three arms relative to the material, comprising:

the arms are swingable about an axis in a plane vertical to the track of the material and the rotary movement for the driven rotation elements is provided by a shaft coaxial with the swing axis and is transferred to the rotation elements via a miter gear attached to the arms;

said arms including lever projections facing away from the semifinished material, said projections being connected to each other by bar structures for enabling common adjustment and setting of the arms;

motor-driven adjustment means connected to one of said arms for a common adjustment and setting of the arms; and a drive engaging, on one hand, one of the lever projections and on the other hand a lever, which lever is pivoted directly at the mounting body and is pressed by a spring arrangement towards a stop in a sense setting the rotation elements.

2. Driver as in claim 1, in which the three arms are arranged at an angular distance of 120 degrees to each other and each have a driven rotation means.

3. Driver as in claim 1, in which a pressure cylinder for setting the rotation elements to the material is connected in series with the adjustment means.

4. Driver as in claim 1, in which a spring arrangement for pressing the rotation elements onto the material is connected in series with the adjustment means.

5. Driver as in claim 1, in which the force of the spring arrangement is adjustable.

6. Driver as in claim 1, in which the lever is connected to the mounting body over a pressure cylinder.

7. Driver as in claim 1, in which the side of the lever is in engagement with the spring arrangement and directly attached to the mounting body.

8. Driver as in claim 1, in which the rotation elements include belt drivers with two rollers having parallel axles, said rollers being wrapped by an endless belt, one of which rollers operates as a driving roller, the other roller as a guide roller.

9. Driver as in claim 8, in which there are additionally provided at least one supporting roller between the driving roller and guide roller.

* * * * *

UNITED STATES PATENT AND TRADEMARK OFFICE
CERTIFICATE OF CORRECTION

PATENT NO. : 4,566,585
DATED : January 28, 1986
INVENTOR(S) : ULRICH DREHER and HELMUT REITZ It is certified that error appears in the above-identified patent and that said Letters Patent is hereby corrected as shown below:

Title page, the Assignee's name should read "INSTITUT DR. FRIEDRICH FÖRSTER PRÜFGERÄTEBAU GmbH & Co KG"

Title page, the Foreign Application Priority Date should be " June 11, 1982 "

Signed and Sealed this

Eighth Day of July 1986

[SEAL]

Attest:

DONALD J. QUIGG

Attesting Officer

Commissioner of Patents and Trademarks